United States Patent [19]

Braden et al.

[11] Patent Number: 4,791,150

[45] Date of Patent: Dec. 13, 1988

[54] COMPOSITION FOR USE IN MAKING BONE CEMENT

[75] Inventors: Michael Braden, Hertfordshire; Laurence G. Wood, Surrey, both of England

[73] Assignees: Bonar Cole Polymers Limited, Surrey; The London Hospital Medical College, London, both of England

[21] Appl. No.: 913,311

[22] Filed: Sep. 30, 1986

[30] Foreign Application Priority Data

Oct. 1, 1985 [GB] United Kingdom ............... 8524152

[51] Int. Cl.[4] .................. A61K 6/08; C08K 3/10; C08L 31/02
[52] U.S. Cl. ................................ 523/117; 523/116; 524/413; 524/423; 524/432; 524/560; 525/309
[58] Field of Search .............. 523/117, 116; 524/413, 524/423, 432, 560; 525/309

[56] References Cited

U.S. PATENT DOCUMENTS

| 3,715,331 | 2/1973 | Molnar ............................ 523/117 |
| 4,389,507 | 6/1983 | Podszun et al. ................ 524/460 |
| 4,404,327 | 9/1983 | Crugnola et al. .............. 525/228 |
| 4,456,711 | 6/1984 | Pietsch et al. ................. 523/206 |
| 4,490,497 | 12/1984 | Evrard et al. .................. 524/349 |
| 4,500,658 | 2/1985 | Fox ................................... 523/117 |
| 4,547,390 | 10/1985 | Ashman et al. ............ 523/117 X |
| 4,617,327 | 10/1986 | Podszun ......................... 523/116 |

FOREIGN PATENT DOCUMENTS

| 0041614 | 5/1981 | European Pat. Off. . |
| 1431211 | 4/1976 | United Kingdom . |
| 2069517 | 8/1981 | United Kingdom . |
| WO82/01006 | 4/1982 | World Int. Prop. O. . |

Primary Examiner—Theodore E. Pertilla
Attorney, Agent, or Firm—Nixon & Vanderhye

[57] ABSTRACT

A composition for forming a bone cement or the like, comprising a powder component and a monomer component, the powder component comprising ethylmethacrylate polymer beads incorporating particles of opacifier therein and the monomer component comprising n-butyl methacrylate.

6 Claims, 1 Drawing Sheet

COMPOSITION FOR USE IN MAKING BONE CEMENT

It is necessary to attach an implant such as a hip prosthesis to living bone by a bone cement. The cements are typically polymeric materials and the surgeon usually mixes the interactive components to make the cement at an appropriate stage during the surgical procedure. Polymers are relatively radiolucent and since the surgeon will later wish to inspect the implant by x-rays it is known to add to the polymers radiopaque materials, herein called opacifiers, examples being barium salts such as barium sulphate, zirconium oxide and zinc oxide. These opacifiers are usually added to polymer beads by the surgeon when he makes up the bone cement and while they give the necessary radiopacity, it has been observed that they tend to reduce the mechanical properties e.g. transverse strength and compressive strength of the set polymeric bone cement. U.S. Pat. No. 4,500,658 points out this observation and describes a method of incorporating an opacifier in an acrylic resin by a suspension polymerisation.

It is one object of the invention to provide a composition for use in making a bone cement which incorporates an opacifier, will provide a cement of enhanced mechanical properties and which additionally is less likely to do damage to the patient.

According to one aspect of the invention there is provided a composition for use in making a bone cement or the like, the composition comprising a powder polymer component and a monomer component therefor, the components being sterile for medical use, an opacifier being incorporated within the polymer of the powder component, characterized in that the polymer is ethylmethacrylate polymer and the monomer comprises n-butyl methacrylate.

With the system of the invention the ethylmethacrylate polymer dissolves almost completely in the n-butyl methacrylate monomer and when the materials are reacted the exothermic heat generated is much reduced. In addition there is little release of monomer, and the formed cement has several improvements in mechanical properties such as an elongation at fracture of about 25%
an improved flexural fatigue strength
a reduced modulus of elasticity When during surgery a bone cement is made up and inserted into the body a drop in the patients blood pressure can occur. The reasons for this are not clear, but it is believed that monomer released from the setting cement during polymerisation is a factor. It has been observed that in the case of the composition of the invention relatively little monomer is released, and clinical data suggest that there is a noticable absence of blood pressure drop and no changes in patients pulse rate were observed.

The monomer component preferably comprises the liquid monomer and an activating tertiary amine. The monomer will be n-butyl methacrylate but other monomers may be present in minor proportions e.g. methylmethacrylate. The amine may be an aniline or toluidine, examples being N,N'-dimethyl p-toluidine, dihydroxyethyl-o-toluidine, dimethyl aniline or diethylaniline. The activator is preferably selected so that polymerisation takes place at or below body temperature.

The particles of the opacifier are substantially uniformly encapsulated within the polymer beads making up the powder component and this distribution provides the necessary radiopacity coupled with the desired mechanical strength in the formed polymer bead and ultimately in the formed bone cement.

The invention further includes a method of making a powder component as defined above, the method comprising dispersing particles of the opacifier with a prepolymer by ball, high speed or similar milling, diluting the dispersion with monomer and carrying out suspension polymerisation to form polymer beads containing particles of opacifier. The beads may be recovered and used directly as the powder component without the addition of further opacifier, although an initiator such as benzoyl peroxide may be added and, as indicated below, other additions are possible.

The physical properties of the polymer and the monomer should be selected for optimum effect according to the intended use. The ethylmethacrylate polymer should have an average molecular weight should range from about 150,000 to about 1,500,000 and the particle size should be distributed in the range of about 15 to 100 micron.

The opacifier may be selected from any of those known for this purpose. Examples are barium sulphate, zinc oxide and zirconium dioxide. The proportions of opacifier may range from about 5 to 50% by weight of the polymer of the powder.

The polymer and monomer will require to be sterilised for surgical use. While different forms of sterilisation may be adopted, it is preferred to sterilise the powder by gamma irradiation and the monomer by bacteriological filtration.

The polymer beads may be made including a peroxide as catalyst and chain transfer agents such as lauryl mercaptan and trichloroethylene may be present. The aqueous phase of the suspension polymerisation may include polyvinyl alcohol and sodium or ammonium polymethacrylate and inorganic stabilisers such as talc or tricalcium phosphate. The powder component may be used directly or additions may be made. For example, extra catalyst may be added to achieve a desired curing time and cross linking agents may be present. Antibiotics may be added, colourants may also be present.

The object to be implanted may take a wide variety of forms and may be placed at for example the hip or knee. Thus for a hip replacement it may be a double cup cup type of prosthesis or the Muller prosthesis. The composition of the invention may however be used for any biomedical application e.g. devices, dentures, implants and the like.

According to other aspects of the invention there is provided for use in making a bone cement or the like, a sterilised powder component comprising a polymethacrylate, preferably a poly (ethylmethacrylate) having a molecular weight in the range of about 150,000 to 1,500,000, the polymer being in the form of beads having a particle size distribution in the range of about 15 to 100 micron, particles of an opacifier having been incorporated within the beads by ball, high speed or similar milling; and a sterilised monomer component comprising n-butyl methacrylate monomer in liquid form and a tertiary amine activator such as N,N'-dimethyl p-toluidine, optionally with a cross linking agent such as ethylene glycol dimethacrylate.

Figure 1:
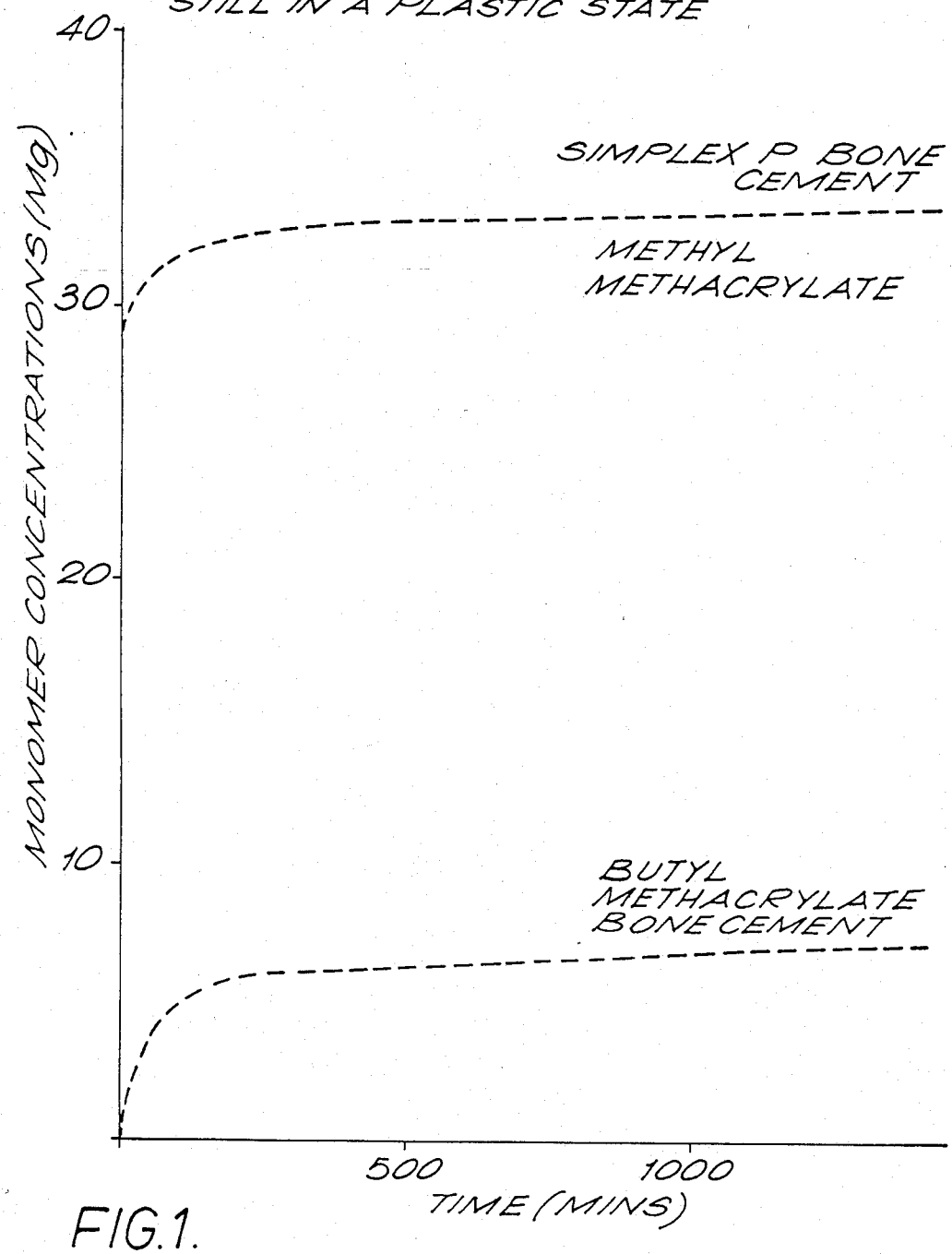
FIG. 1 shows that the loss of monomer in the case of the n-butyl methacrylate in bone cement is substantially less than that of methyl methacrylate.

The invention is illustrated by the following non-limitative examples:

EXAMPLE 1

A prepolymer syrup was prepared by charging the following to a suitable vessel equipped with a heating-/cooling jacket, stirrer and reflux condenser
ethyl methacrylate monomer: 80 kg
azoisobutyronitrile: 6 g
lauryl mercaptan: 200 g The mix was heated with slow agitation to 80° to 100° C. and held at that temperature for three hours. The polymer content was checked, the charge cooled and sufficient ethyl methacrylate monomer added to achieve a polymer content of ca. 10%. The composition was charged to a ball mill and as follows
prepolymer syrup (prepared above): 30 kg
barium sulphate (pharmaceutical grade): 15 kg
dispersing aid: 0.3 g
and ground for about 18 to 24 hours. To a suspension polymer reactor equipped with a heating/cooling jacket, stirrer and reflux condenser there was added
de-ionised water: 60 kg
polyvinylpyrollidone: 0.4 kg
and the mix was heated to 60° C. with stirring. There was then added
ball milled syrup (prepared above): 10 kg
ethyl methacrylate monomer: 25 kg
benzoyl peroxide: 0.5 kg The heating at 80° C. was continued for 5 hours, the mix cooled and the bead polymer was recovered by filtration washing with water and drying. The formed polymer component was subjected to reaction with n-butyl methacrylate monomer component including N,N'-dimethyl-p-toluidene as activator to form a set bone cement.

The following observations were made:
(i) exothermic temperature rise due to heat of polymerisation: about 50° C. (maximum)
(ii) properties of set composition relative a polymethylmethacrylate system in which barium sulphate was hand blended, control=1.
ductility in tension at room temperature: 10.5
toughness in tension at room temperature: 9.2
toughness in impact at 37° C.: 1.0
fatigue resistance at room temperature: 30.0

These results show that the cement of the invention causes a substantially reduced polymerisation exotherm resulting in less damage to body tissue. The set cement is ductile and not brittle, has a substantially improved flexural fatigue life, a lower modulus of elasticity and improved absorption of shock waves. In surgical evaluations it was observed that the set cement could be removed by cutting with a reciprocating saw, an osteotome or by remaining and was thus able to be used in revisions of operations.

EXAMPLE 2

The loss of free monomer from a setting bone cement composition of the invention according to Example 1 was compared with that from a known bone cement, a "Simplex P" bone cement. Samples of both cements were made up and while still in the plastic state were immersed in saline solution. Aliquots were taken and monomer released was measured by high performance liquid chromotography. The results are shown in the graph of FIG. 1 from which it can been seen that the loss of monomer in the case of the n-butyl methacrylate is substantially less than that of methyl methacrylate. As a result there is less likelihood of loss of blood pressure during surgery.

What is claimed is:

1. A composition for use in making a bone cement, the composition comprising a powder polymer component and a monomer component therefor, the components being sterile for medical use, an opacifier being incorporated within the polymer powder component, wherein the polymer is ethylmethacrylate polymer and the monomer is n-butyl methacrylate, whereby on polymerization of polymer and monomer little monomer is released on setting.

2. A composition according to claim 1, wherein the ethylmethacrylate polymer has an average molecular weight range from about 150,000 to about 1,500,000 and a particle size distribution in the range of about 15 to 100 micron.

3. A composition according to claim 1, wherein the monomer component comprises the liquid monomer and an activating tertiary amine and is selected so that polymerisation takes place at or below body temperature.

4. A composition according to claim 1, wherein the ehtylmethacrylate polymer is sterilised by gamma irradiation and the monomer by bacteriological filtration.

5. A composition according to claim 1, wherein the opacifier is barium sulphate, zinc oxide or zirconium dioxide in a proportion of from about 5 to 50% by weight of the polymer of the powder.

6. A powder component consisting essentially of sterilised poly (ethylmethacrylate) having a molecular weight in the range of about 150,000 to 1,500,000, the polymer being in the form of beads having a particle size distribution in the range of about 15 to 100 micron, and particles of an opacifier incorporated within the beads by ball, high speed or like milling.

* * * * *